United States Patent [19]

Namiki

[11] Patent Number: 5,792,479
[45] Date of Patent: Aug. 11, 1998

[54] TECHNIQUE FOR ACCELERATION OF APOPTOTIC CELL DEATH

[75] Inventor: Hideo Namiki, Tokyo, Japan

[73] Assignee: Discovision Associates, Irvine, Calif.

[21] Appl. No.: 771,553

[22] Filed: Dec. 11, 1996

Related U.S. Application Data

[62] Division of Ser. No. 510,017, Aug. 1, 1995, abandoned.

[30] Foreign Application Priority Data

Aug. 16, 1994 [JP] Japan .................. 6-192403

[51] Int. Cl.$^6$ .................................. A61K 35/16
[52] U.S. Cl. .......................... 424/531; 514/561
[58] Field of Search ................. 435/240.1, 240.2, 435/240.3; 424/531; 514/561

[56] References Cited

U.S. PATENT DOCUMENTS

| | | | |
|---|---|---|---|
| 4,533,637 | 8/1985 | Yamane et al. | 435/240 |
| 5,248,606 | 9/1993 | Walsh et al. | 435/240.4 |
| 5,272,082 | 12/1993 | Santoli et al. | 435/240.2 |
| 5,298,407 | 3/1994 | Anderson et al. | 435/69.1 |
| 5,360,893 | 11/1994 | Owens et al. | 530/350 |
| 5,387,520 | 2/1995 | Lopresti et al. | 435/240.2 |
| 5,468,624 | 11/1995 | Thompson et al. | 435/69.1 |
| 5,476,659 | 12/1995 | Goodman et al. | 434/278.1 |

FOREIGN PATENT DOCUMENTS

| | | |
|---|---|---|
| 270719 | 10/1990 | Japan . |
| 96651 | 4/1992 | Japan . |

OTHER PUBLICATIONS

Erdoe et al., Mol. Neuropharmacol. 2(3): 245–247 (1992) Abstract.

Bissonnette, R.P., F. Echeverri, A Mahboubi, D.R. Green, Apoptotic Cell Death Induced by C–MYC is Inhibited by BCL–2,Nature, vol. 359, Oct. 8, 1992.

Cain, K., S.H. Hussain, L. Kokileva, G.M. Cohen, Multi-Step DNA Cleavage in Rat Liver Nuclei is Inhibited by Thiol Reactive Agents, FEBS Letters, vol. 358, 255–2611 1995.

Cohen, J.J., R.C. Duke, Apoptosis and Programmed Cell Death in Immunity, Annual Review of Immunology, vol. 10, 267–293 1992.

Coles, H.S.R., J.F. Burne, M.C. Raff, Large–Scale Normal Cell Death in the Developing Rat Kidney and Its Reduction by Epidermal Growth Factor, Development, vol. 118, 777–784 (1993).

Eastman, A., Highlights Apoptosis: A Product of Programmed And Unprogrammed Cell Death, Toxicology and Applied Pharmacology, vol. 121, 160–164 1993.

Endresen, P.C., T.J. Eide, J. Aarbakke, Cell Death Initiated by 3–Deazaadenosine in HL–60 is Apoptosis and is Partially Inhibited by Homocysteine, Biochemical Pharmacology, vol. 46, No. 11, 1893–1901 1993.

Endresen, P.A., P.S. Prytz, S. Lysne, J. Aarbakke, Homocysteine Increases the Relative Number of Apoptotic Cells and Reduces the Relative Number of Apoptotic Bodies in HL–60 Cells Treated with 3–Deazaadenosine, The Journal of Pharmacology and Experimental Therapeutics, vol. 269, No. 3, 1245–53 1994.

Evan, G., A Wyllie, C. Gilbert, T. Littlewood, H. Land, M. Brooks, C. Waters, L. Penn, D. Hancock, Induction of Apoptosis in Fibroblasts by C–MYC Protein, Cell, vol. 69, 119–128 Apr. 3, 1992.

Fanidi, A., E. Harrington, G. Evan, Cooperative Interaction Between C–CMYC and BCL–2 Proto–Oncogenes, Nature, vol. 59, Oct. 8, 1992.

Henderson, S., M. Rowe, C. Gregory, D. Carter, F. Wang, R. Longnecker, E. Kieff, A. Rickinson, Induction of BCL–2 Expression by Epstein–Barr Virus Latent Membrane Protein 1 Protects Infected B Cells From Programmed Cell Death, Cell, vol. 65, 1107–1115 Jun. 28, 1991.

Kurita, T., H. Namiki, Comparison of Cytoxicity Among Sera From Various Sources, Cytologia, vol. 58, 445–452 1993.

Kurita, H., H. Namiki, Serum Induced Cell Death, Zoological Science, vol. 10, 431–438 1993.

Kurita, T., H. Namiki, Apoptotic Cell Death Induced by Serum and Its Prevention by Thiols, Journal of Cellular Physiology, vol. 161(1), 63–70 1994.

Meister, A., S. Tate, Glutathione and Related Y–Glutamyl Compounds: Biosynthesis and Utlization, Annual Review of Biochemistry, vol. 45, 559–604 1976.

Rouach, E., D. Resnitsky, J. Lotem, L. Sachs, A. Kimchi, M. Oren, Wild–Typ P–53 Induces Apoptosis of Myeloid Leukemic Cells That is Inhibited by Interleukin–6, Nature, vol. 352, Jul. 25, 1995.

Rubartelli, A., N. Bonifaci, R. Sitia, High Rates of Thioredoxin Secretion Correlate with Growth Arrest in Hepatoma Cells, Cancer Research, vol. 55, 675–680, Feb. 1, 1995.

Wyllie, A.H., J.F.R. Kerr, A.R. Currie, Cell Death: The Significance of Apoptosis, Internal Review of Cytology, vol. 68, 251–306 1980.

Ziegler, D.M., Role of Reversible Oxidation–Reduction of Enzyme Thiols–Disulfides in Metabolic Regulation, Annual Review of Biochemistry, vol. 54 305–329 1985.

*Primary Examiner*—Jean C. Witz
*Attorney, Agent, or Firm*—Ronald J. Clark; Robert T. Braun; Arthur S. Bickel

[57] ABSTRACT

A first embodiment of a cell culture system has a cell death accelerator comprising one or more cell death inducing substances, including serum albumin, hemoglobin, glycine and glutamic acid. In a second embodiment a cell death inhibitor comprises one or more kinds of cell death inhibiting substances which include mercapto group containing amino acids, other mercapto group containing compounds and tryptophan. In a third embodiment a cell death inhibitor comprises an inhibitor of RNA or protein synthesis, optionally augmented with a thiol. The system can be applied to selectively induce death of cultured cells, such as neoplastic cell lines, or to inhibit death of other cells, such as neoplastic cell lines or non-neoplastic cells such as brain cells.

11 Claims, 6 Drawing Sheets

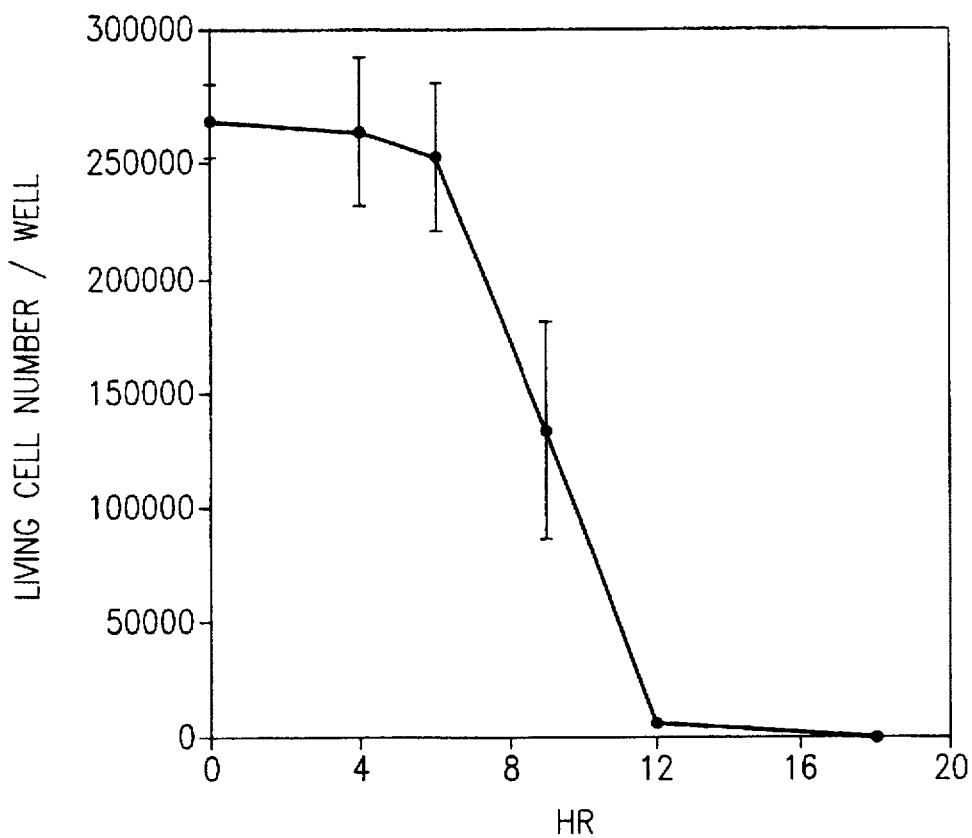
FIG.8
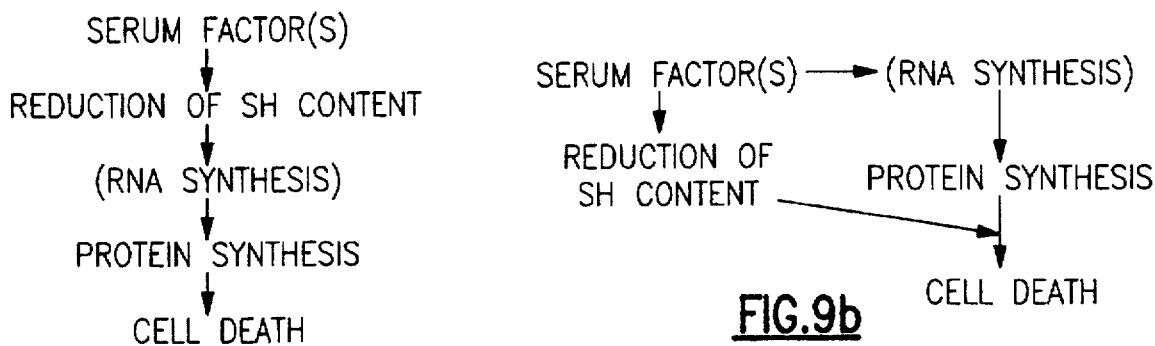
FIG.9a
FIG.9b

TECHNIQUE FOR ACCELERATION OF APOPTOTIC CELL DEATH

This is a divisional of application Ser. No. 08/510,017 filed on Aug. 1, 1995, now abandoned.

BACKGROUND OF THE INVENTION

1. Field of the Invention.

This invention relates to a cell death accelerator for inducing cell death and a cell death inhibitor for inhibiting cell death.

2. Description of the Related Art.

For the purpose of culturing cells in vitro, serum is generally added to a synthetic culture medium in a concentration range of about 10–20%. The medium is a pH-balanced salt solution containing various nutrients such as vitamins, amino acids, and sugars. When serum or plasma is highly concentrated in the medium, beyond this range however, cell death is induced.

The cell death-inducing activity is seen in all the sera or plasma so far tested regardless of source (species or age), or heat treatment to inactivate complement. Two types of cell death are now generally recognized. The first is passive, resulting from lack of oxygen, mechanical crush injury, or other extreme change in the extracellular environment. The second type of cell death is called apoptosis, an active energy-requiring intracellular process that culminates in DNA fragmentation and osmotic lysis of the cell. The latter is an autonomous physiological death sometimes referred to as programmed cell death, and it occurs normally during development of the nervous system, skin, and other epithelial organs. Morphologically, apoptosis is characterized by blebbing of the plasma membrane and nuclear condensation. These visible changes are accompanied by synthesis of a specific protein(s) including nuclease followed by fragmentation of chromosomal DNA Several apoptosis-related genes have already been identified in the nematode C. elegans and in mammalian lymphocytes.

Apoptosis is now the focus of much attention, because it appears to be crucial for normal tissue and organogenesis, neural development, and immune reactions to foreign antigens including those borne by infectious viruses.

The serum contains some components, i.e., proteins such as albumin and globulin, salts such as NaCl, KCl and $CaCl_2$, vitamins, more than twenty amino acids, such as glycine, cystine, cysteine, alanine and tryptophan, and other components. Heretofore adequate investigation of the individual functions of each component in the serum has not been carried out. The present inventors disclosed that amino acids, such as cystine and cysteine, when added to the serum, decrease the toxic effect of the serum and accelerates growth and/or multiplication of cultured cells in Japanese Patent Application No. 270719/1990 filed on Oct. 9, 1990. At present, however, investigation of the toxic factor itself has not been carried out at all, and the characterization of components which can inhibit the toxicity has been insufficient. In the noted Japanese Application, the inventors disclosed that cysteine and cystine promoted cell growth and/or multiplication, and that tryptophan can prevent cell death.

Recently, Evan et al. (1992) reported that cultured fibroblasts died when the mitotic cycle was interrupted during c-myc expression. Serum-induced cell death may involve a similar mechanism. Cells entering the mitotic cycle in response to an excess of growth signals from serum may die after interruption of the cycle by thiol deficiency. Previously, we reported that a cell-death-inducing activity was present in a low molecular weight fraction of serum (M.W.<1,000) (Kurita and Namiki, 1993a). Subsequently, it was found that this activity was inhibited by thiols. It was water-soluble, heat-resistant, and had charcoal affinity. Approximate molecular weight of the factor was approximately 100–200 dalton upon size-sieve HPLC. In addition to low molecular weight factors, traces of macromolecules in the fraction are now thought to be necessary for cell death. The latter may act as a death signal, and c-myc may be also involved in the signal transduction. Further studies are needed to address these issues. Nevertheless, serum-induced cell death appears to be a type of apoptosis resulting from a disturbance in thiol metabolism.

SUMMARY OF THE INVENTION

Under the above mentioned circumstances, we have investigated the functions of individual components in the serum, and have achieved the present invention on the basis of the results of the investigation.

It is an object of the present invention to provide a cell death accelerator for inducing cell death.

It is another object of the present invention to provide a cell death inhibitor for inhibiting cell death.

According to a first aspect of the invention, a cell death agent comprises at least one cell death inducing substance which is selected from serum albumin, hemoglobin, glycine and glutamic acid to be added to blood. Cell death of cultured cells is produced by adding one or more of the above mentioned substances to a culture medium containing serum. For example, the cell death accelerator of the invention can be applied to treat cancer because the cell death inducing substance destroys cancer cells or inhibits growth and/or multiplication of cancer cells.

According to a second aspect of the invention, a cell death inhibitor comprises at least one cell death inhibiting substance which is selected from mercapto group containing amino acids such as cysteine, cystine and so forth, other mercapto group containing compounds and tryptophan, the selected substance to be added to blood.

The cell death inhibiting substances in the serum are mercapto group containing amino acids, other mercapto group containing compounds and tryptophan. When one or more of the above mentioned cell death inhibitors are added to a culture medium containing serum, the inhibitors counteract the toxic effects of the toxic factor in the serum, and, thereby the cell death of cultured cells is inhibited. For example, if the cell death inhibiting substances are added to an instillation injection, and then injected into the central nervous system of a patient, and directly supplied to a diseased part during treatment of brain apoplexy, eye ground apoplexy and so forth, death of the patient's cells can be prevented efficiently.

We had previously found that various sera supplemented with amino acids and vitamins in quantities equivalent to those in basal tissue culture medium inhibited cell growth but did not induce cell death. Herein we disclose the identity of the rescue factors as L-cysteine or L-cystine and L-tryptophan, and we examine the effects of thiol-containing molecules other than L-cysteine on serum induced cell death. All of them were protective in varying degrees. Death is also prevented by several inhibitors of protein and RNA synthesis. Interestingly, N-acetyl-L-cysteine (NAC) was as protective as other thiols, but it did not inhibit uptake of L-[$^{35}$S]methionine, suggesting that thiol bearing molecules were not acting as inhibitors of protein or RNA synthesis. Treatment of cells cultured in FBS with NAC prevented a reduction in their thiol content, but protein and RNA synthesis inhibitors had no corresponding effect. In addition, we also demonstrated DNA fragmentation prior to the breakdown of the plasma membrane. These findings suggest that serum-induced cell death represents a thiol-mediated apoptosis.

The invention provides a cell system which includes a concentration of a low molecular weight fraction of serum. A population of living cells are exposed to the serum, and optionally to a concentrated and refined molecular species that prevents induction of death of the cells by whole serum. The cells can be human fetal lung fibroblasts, human epithelioid carcinoma cells, or mouse melanoma cells.

According to an aspect of the invention the molecular species is a thiol or a dithiol homo-dimer thereof. The molecular species can be at least one of the group consisting of cysteine, glutathione, dithiothreitol, 2-mercaptoethanol, dithionite, thioglycolic acid, DL-homocystine, N-acetyl-L-cysteine, 5,5'-dithiobis(2-nitrobenzoic acid), a homo-dimer thereof, and a mixed disulfide thereof.

Preferably the molecular species has a concentration of between about 1 and 10 mM.

The invention provides a cell system which includes a concentration of serum. A population of living cells are exposed to the serum, for example fetal bovine serum, and to a concentrated and refined molecular species that accelerates induction of death of the cells. The molecular species is selected from the group consisting of serum albumin, hemoglobin, glycine and glutamic acid. The cells can be human fetal lung fibroblasts, human epithelioid carcinoma cells, or mouse melanoma cells.

The invention provides a method of preventing cell death in a cell system which is accomplished by providing a concentration of a low molecular weight fraction of serum, which is equivalent to a cytotoxic concentration of whole serum, the latter being sufficient to induce cell death, exposing a population of living cells to the low molecular weight serum fraction, and optionally exposing the living cells to a concentrated and refined molecular species that prevents induction of death of the cells by the serum. The cells can be human fetal lung fibroblasts, human epithelioid carcinoma cells, or mouse melanoma cells. According to an aspect of the invention the molecular species is a thiol or a dithiol homo-dimer thereof. The molecular species can be at least one of the group consisting of cysteine, glutathione, dithiothreitol, 2-mercaptoethanol, dithionite, thioglycolic acid, DL-homocystine, N-acetyl-L-cysteine, 5,5'-dithiobis (2-nitrobenzoic acid), a homo-dimer thereof, and a mixed disulfide thereof.

Preferably the molecular species has a concentration of between about 1 and 10 mM.

The invention provides a method of preventing serum-induced apoptotic cell death, which is accomplished by providing a cell culture medium which has a concentration of a low molecular weight fraction of serum, which is equivalent to a cytotoxic concentration of whole serum, the latter being sufficient to induce cell death, enriching the medium with an amino acid selected from the group consisting of L-cysteine, L-cystine, and L-tryptophan, and culturing a cell line in the enriched medium.

According to an aspect of the invention the amino acid is L-cysteine in a concentration of between about 0.1 mM and 5 mM.

In another aspect of the invention the amino acid is L-cystine in a concentration of between about 0.05 mM and 0.5 mM.

The invention provides a method of preventing serum-induced apoptotic cell death, which is performed by providing a cell culture medium has a cytotoxic concentration of serum, enriching the medium with a substance selected from the group consisting of puromycin hydrochloride, emetine hydrochloride, cycloheximide, actinomycin D, ethidium bromide, L-tryptophan, and D-tryptophan, and culturing a cell line in the enriched medium.

According to an aspect of the invention the medium is enriched with a thiol, which can be N-acetyl-cysteine.

The invention provides a method of preventing serum-induced apoptotic cell death, which is performed by providing a cell culture medium having a cytotoxic concentration of serum, culturing a cell line in the enriched medium, and while the cells are growing in culture, inhibiting protein synthesis or RNA synthesis in the cell line.

BRIEF DESCRIPTION OF THE DRAWING

For a better understanding of these and other objects of the present invention, reference is made to the detailed description of the invention, by way of example, which is to be read in conjunction with the following drawings, wherein:

FIG. 8 is a chart illustrating the relationship of live cultured cells to time in an experiment on serum toxicity; and FIGS. 9a and 9b are schematic illustrations of two models of serum-induced cell death.

DESCRIPTION OF THE PREFERRED EMBODIMENT

Abbreviations

As used herein certain abbreviations and acronyms have the following meanings:

| ACT D | actinomycin D | FBS | fetal bovine serum |
|---|---|---|---|
| CHX | cycloheximide | GSH | glutathione reduced |
| CYS | cysteine | GSSG | glutathione oxidized |
| CYS-CYS | cystine | 2-ME | 2-mercaptoethanol |
| DL-HC | DL-homocystine | NAC | N-acetyl-L-cysteine |
| DTN | sodium dithionite | NON | non-inhibitor |
| DTNB | 5,5'dithiobis(2-nitrobenzoic acid) | PBS | Phosphate buffered saline |
| | | PMC | puromycin.2HCl |
| DTT | dithiothreitol | TGA | thioglycolic acid |
| EAA | essential amino acids | MEM | minimal essential medium |
| EMT | emetine.2HCl | NEAA | nonessential amino acids |
| ET Br | ethidium bromide | | |

In one experiment, a cell system had a cytotoxic concentration of serum sufficient to induce cell death. A population of living cells was exposed to the serum, and a concentrated and refined molecular species that prevents induction of death of the cells by the serum was included in a culture medium. Suitable cells were human fetal lung fibroblasts, human epithelioid carcinoma cells, and mouse melanoma cells. More particularly TIG-cells, i.e., human fetal lung fibroblasts, were seeded into a 96-well multiplate ($1 \times 10^4$ cells/well) and incubated overnight. Thereafter the culture medium was removed to be exchanged with test medium, a culture medium containing fetal bovine serum (FBS) and various selected reagents. Six days after the exchange of the culture medium, living cells in the culture medium were counted using a dye elution method to obtain the living cell density associated with each reagent.

The molecular species used was a thiol or a dithiol homo-dimer thereof, or a mixed disulfide in various concentrations which included the range of between about 1 and 10 mM.

The following reagents were used: L-cystine (L-CYSCYS); D-cystine (D-CYSCYS); L-cysteine (L-CYS); D-cysteine (D-CYS); reduced glutathione (GSH); oxidized glutathione (GSSG); DL-homocystine (DL-HC); N-acetyl-L-cysteine (NAC); 2-mercaptoethanol (2-ME); thioglycolic acid (TG); dithiothreitol (DTT); 5-5,5'-dithiobis (2-nitro benzoic acid) (DTNB); sodium dithionite (DTN); and L-tryptophan (L-TRP). The concentration of each reagent was set at four levels: 0.01 mM, 0.1 mM, 1.0 mM and 10 mM.

Figure 1:
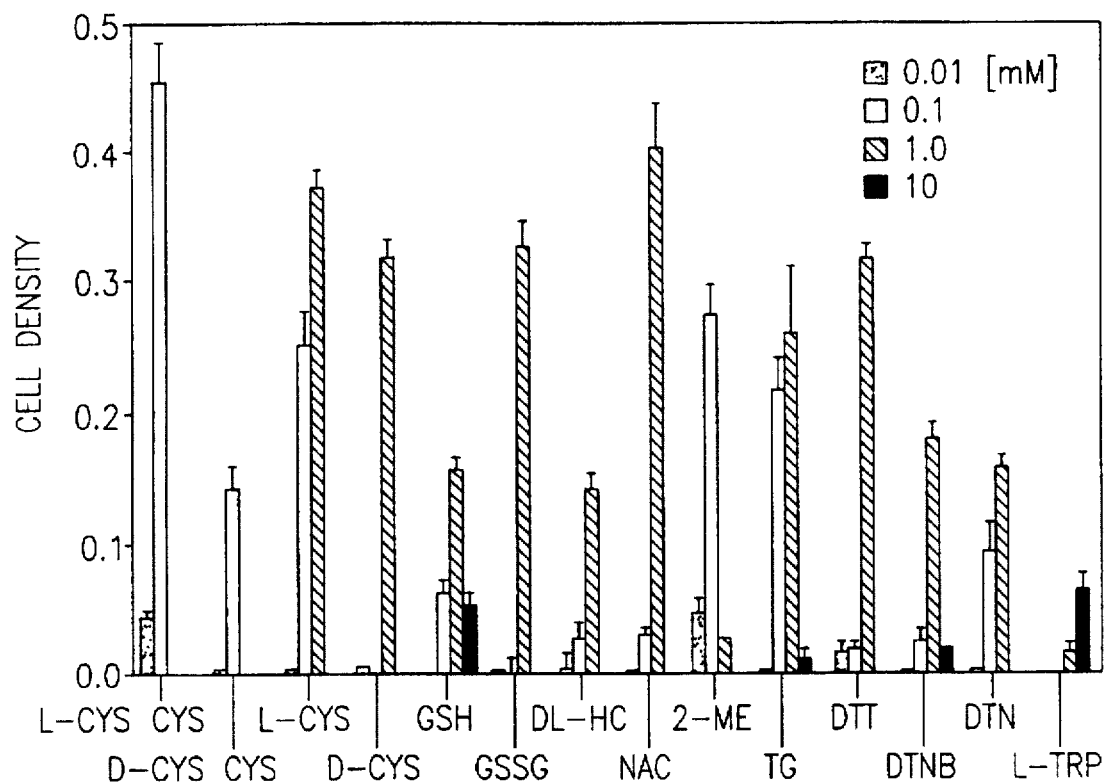
FIG. 1 is a chart showing the cell death inhibiting effects of substances on cultured cells.

A result of the experience is shown in FIG. 1. In FIG. 1, each reagent is indicated along the abscissa and the corresponding cell density is indicated along the ordinate. The height of each column in the graph indicates the mean of the measured cell densities of six wells, and a bar on the top of each column, if shown, indicates the standard error.

According to the result, reagents which had a mercapto group in their chemical structures conduced to inhibition of the cell death. L-CYSCYS, D-CYSCYS, L-CYS, 2-ME, TG and DTN showed greatly inhibiting effects. They could prevent cell death even at a concentration of I mM. It was recognized that mercapto group containing amino acids and other mercapto group containing compounds could inhibit cell death.

Experiments on cell death inducing substances which exist in serum will now be explained. A cell system was used which had a cytotoxic concentration of serum sufficient to induce cell death. A population of living cells was exposed to the serum, and the culture medium contained a concentrated and refined molecular species that accelerates induction of death of the cells by the serum. The molecular species was one of the group consisting of serum albumin, hemoglobin, glycine and glutamic acid. Suitable cells were human fetal lung fibroblasts, human epithelioid carcinoma cells, and mouse melanoma cells.

A low molecular weight fraction in FBS serum was freeze-dried, and a solvent then added. The insoluble fraction in was removed by centrifugation to purify the low molecular weight fraction. The soluble fraction thereby obtained was freeze-dried again, and washed in acetonitrile. The resulting freeze-dried substance was dissolved in distilled water to prepare a sample solution having an approximately 20-fold dilution of the low molecular weight fraction with respect to FBS, supposing that recovery of the low molecular weight fraction therefrom is 100%. Thereafter, the sample solution was filtered through a filter having a 0.2μ mesh.

This sample solution was added to Hank's solution so as to obtain a test medium containing 10 volume % of above mentioned sample solution, 1 volume % of FBS and 10 volume % of MEM. Further, each reagent or combination of the reagent and cysteine being tested was added to the test medium at reagent concentrations of 1 mM and 10 mM.

TIG-cells were seeded into a 24-well multiplate ($5 \times 10^3$ cells/well) having the test medium and incubated for 48 hours. Thereafter living cell density was measured using the dye elution method.

According to the experimental results, glycine, glutamic acid and tryptophan showed a cell death inducing effect at 1 mM. Phenylalanine, aspartic acid, asparagine and glutamine also showed a cell death inducing effect at 10 mM. On the other side, thyrosin, serine and glycylglycine did not show a cell death inducing effect, but inhibited growth and/or multiplication of cells. It was furthermore proved that hemoglobin had growth and/or multiplication inhibiting effect in the same manner.

These and other experiments will now be disclosed in further detail.

Cell cultures

Human fetal lung fibroblasts (TIG-1), human epithelioid carcinoma (HeLa) cells, and mouse melanoma (B16) cells were obtained from the Japanese Cancer Research Resources Bank. All cells were maintained in Eagle's MEM containing 10% FBS at 37° C. Cell cultures were examined and photographed with a Nikon Diaphot phase-contrast inverted microscope.

Reagents

Amino acids: L-cysteine or L-cystine (Kanto Chemical), D-cysteine (Sigma), D-cystine (Wako), L-tryptophan (Kanto), D-tryptophan, DL-homocystine (Wako), glutathione oxidized form (Sigma grade III), reduced form (Merck), dithiothreitol (Wako), 2-mercaptoethanol, thioglycolic acid, N-acetyl-L-cysteine, sodium dithionite (Kanto), 5,5'-dithiobis(2-nitro benzoic acid) (Kanto), emetine.2HCl (Fluka AG.), cycloheximide, puromycin. 2HCl, actinomycin D, ethidium bromide (Sigma).

Serum and media

FBS was from Boehringer Mannheim (lot. 614413, 562044, 147013). Eagle's MEM "Nissui" was from Nissui Pharmaceutical Co., EAA (essential amino acids) supplement for MEM×50, NEM (nonessential amino acids) supplement for MEM×100 and vitamin supplement for MEM×100 were from Boehringer Mannheim, Flow Laboratories, and Dainippon Pharmaceutical Co., respectively.

Ultrafiltration of FBS

FBS was filtered through an ultrafiltration membrane YM2 (M.W.1,000) (Amicon Co.). FBS was concentrated tenfold and diafiltered with a tenfold volume of deionized water to remove the low-molecular-weight fraction. The resultant macromolecular fraction of FBS was again concentrated tenfold and was diluted to the original FBS volume with 10/9 concentrated Eagle's MEM. pH and osmolality were adjusted to 7.2±0.2 and 290±10 mosmol/Kg.H$_2$O), as the low-molecular-weight-fraction depleted FBS.

Automated cell counting

Appropriate numbers of cells were seeded into 96-well culture plates containing Eagle's MEM, 10% FBS (100

µl/well) (Corning). After overnight incubation at 37° C. in 5% $CO_2$, the culture medium was removed. Wells were washed with calcium and magnesium-free PBS (CMF-PBS), and 100 µl of test medium was added. After several days of incubation, cells were harvested by trypsinization and suspended in Isotone II (Coulter Electronics). Cell number was measured with a Coulter Counter ZM (Coulter Electronics) and displayed numbers were corrected with standard hemocytes. We previously verified that the numbers displayed on the counter were in agreement with those counted using a hemocytometer. Results were expressed as the means (±SE) of six independent measurements.

Cell counting by dye elution method

TIG-1 cells were seeded in 96-well microplates in 100 µl of Eagle's MEM, 10% FBS. After several day's incubation, medium was removed and the cells were washed with CMF-PBS. Cell quantity was determined by the method of Hori et al. (1988) with a minor modification. Cells were stained with 50 µl of 0.5% crystal violet per well in ethanol/water (1:4) for 10 min and then washed with water. The dye was eluted with 150 µl of 33% acetic acid per well, and the absorbance at 600 nm was measured by a microplate reader (CORONA MTP-22). Results were expressed as the means (±SE) of six independent determinations. We preliminarily confirmed that the absorbance at 600 nm was proportional to the density of TIG-1 cells cultured in MEM, 10% FBS.

Cell viability

TIG-1 cells were seeded in 48-well microplates in 100 µl of Eagle's MEM, 10% FBS. After incubation, cells were harvested with 0.1% trypsin, in CMF-PBS, and 0.5% trypan blue in PBS was added. Cells that were not stained were counted with a hemocytometer. Results were expressed as the means (±SE) of four independent determinations.

L-[$^{35}$S]methionine Uptake

TIG-1 cells were seeded into a 24-well multiplate at ½ confluency (about ×10$^5$ cells/well) and incubated overnight. The next morning, the culture medium was removed and changed to test medium (20 µCi L-[$^{35}$S]methionine (Amersham), 20% CMF-PBS, 80% FBS). After appropriate time (0–16 hr) of incubation, each culture was washed three times with 0.02% EDTA CMF-PBS, and the cells were lysed with 1% SDS. Macromolecules were precipitated with each 10 µl TCA and centrifuged, and the precipitate was washed with 10% TCA. Then, it was dissolved in 300 µl of 1% SDS, 100 µl of which was dissolved in 1 ml of liquid scintillation cocktail and counted (Aloka LSC-700).

Thiol Content Assays

TIG-1 cells were cultured in a 24-well plate (3×10$^5$ cells/well) in fresh medium for 24 hr. The medium was then changed to the test medium, MEM plus 10% FBS, Hank's balanced solution, or whole FBS supplemented with various reagents. Total thiol content was determined as follows. After appropriate hr (0–16) of incubation, cells were washed twice with 0.02% EDTA, CMF-PBS, and they were lysed with 200 µl/well of 1% SDS, 0.02% EDTA, 50 mM Tris-HCl (pH.8.2). The lysate was dyed with 10 µl of 20 mM DTNB dissolved in methanol. Pre-chilled ethanol (600 µl) was added to precipitate the macromolecules, and precipitates were collected by centrifugation at 13,000×g for 20 min. Absorbance at 415 nm of the supernatant was measured by a microplate reader (Bio Rad 3550). Concentration of thiol was calculated by comparison to a GSH standard. Ethanol-soluble thiol was measured as follows. After appropriate hr (0–16) of incubation, cells were washed twice with 0.02% EDTA, CMF-PBS, and they were lysed with 100 µl/well of 1% SDS, 0.02% EDTA, 50 mM Tris-HCl (pH.8.2). Macromolecules were precipitated with 300 µl of pre-chilled ethanol, and precipitates were removed by centrifugation at 13,000×g for 20 min. The supernatant was dyed with 10 µl of 20 mM DTNB dissolved in methanol, and the absorbance at 415 nm of the supernatant was measured by a microplate reader. Concentration of thiol was calculated by comparison to a GSH standard. Thiol content was expressed as SH mol/living cell number.

DNA Fragmentation Assay

TIG-1 cells (3.5×10$^5$ cells/35 mm dish) were washed twice with CMF-PBS and lysed in 0.8 ml 0.6% TE buffer with 1 µg/ml Rnase. Then, 200 µl of 5M NaCl was added to the solution and stored at 4° C. overnight, and macromolecular DNA was pelleted by centrifugation at 13,000×g for 30 min. DNA in the supernatant was purified by phenol-chloroform extraction, and traces of phenol were removed by extracting twice with chloroform. Purified DNA was collected by centrifugation at 13,000×g for 20 min with 3M potassium acetate and 70% ethanol. Precipitated DNA was dissolved in TE buffer, and ⅕ to ⅓ volume of the solution was electrophoresed in a 2.6% agarose gel. Gel was stained by 0.5 µg/ml ethidium bromide and photographed in 254 nm ultraviolet.

We previously discovered that most types of cultured cells died in concentrations of serum exceeding 60%. However, low molecular weight fraction-depleted serum whose osmotic pressure was adjusted with Eagle's MEM (UF-FBS) never showed cytotoxicity. The low molecular weight fraction thus filtered was similar to MEM in salt content, but it was deficient in nutrients such as vitamins and amino acids. We therefore enriched FBS with these nutrients equivalent to the amounts present in MEM for cell culture.

Figure 3:
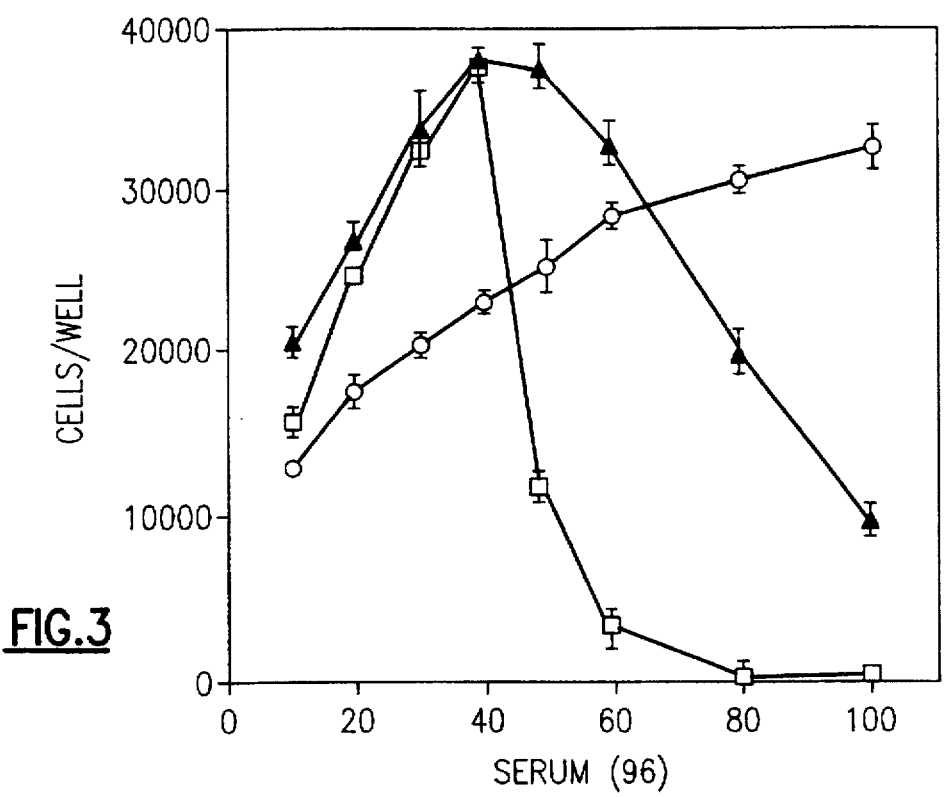
FIG. 3 is a chart indicating the effect of serum concentration on cell growth.
Figure 2:
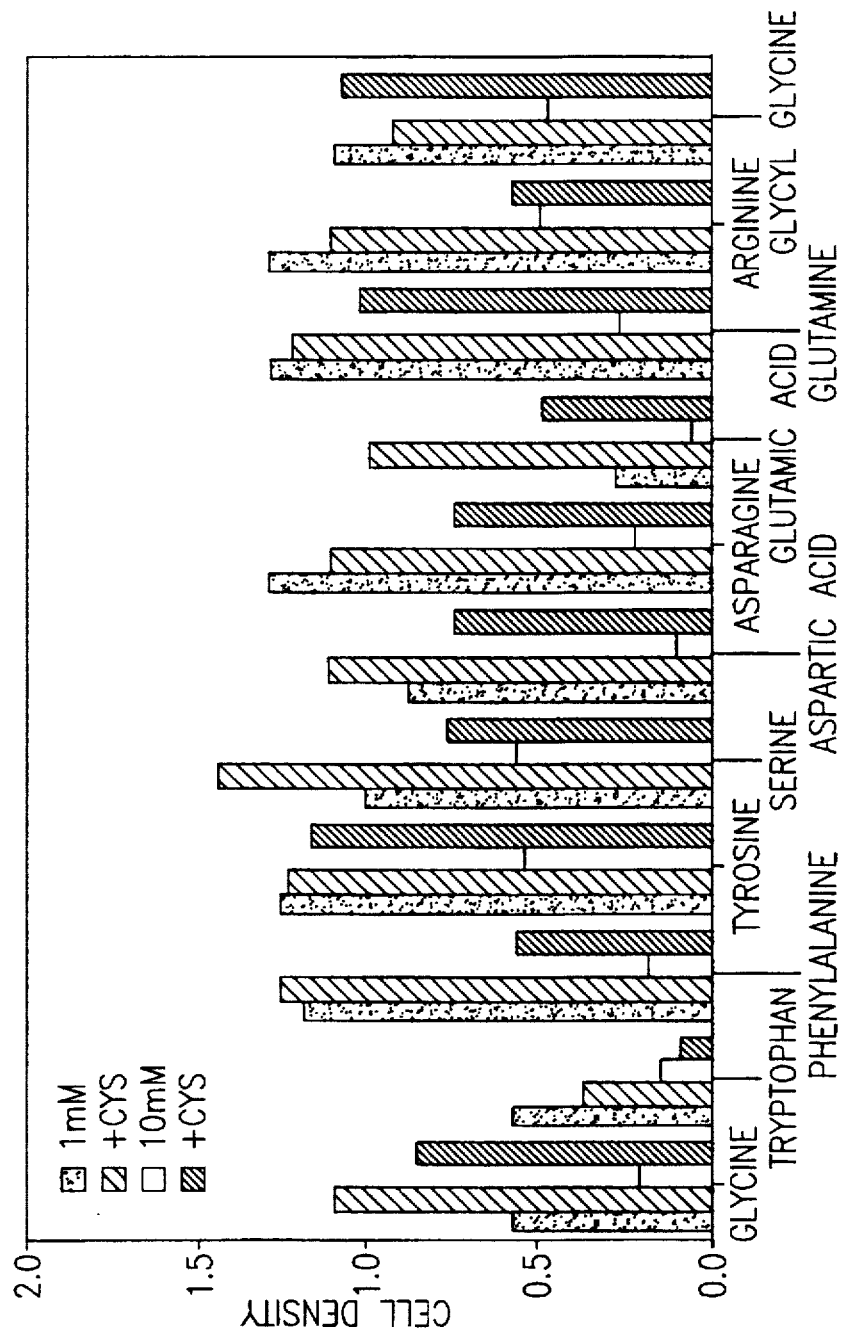
FIG. 2 is a chart showing the cell death inducing effects of substances on cultured cells.

FIG. 3 shows the effect of serum concentration on TIG-1 cell growth, wherein □ indicates Unenriched FBS; ▲ indicates FBS+AA VIT; and ○ indicates low molecular weight fraction-depleted FBS. In developing the data illustrated in FIG. 3, TIG-1 cells were seeded at a density of 5×10$^3$ cells/well in 96-well microplates in Eagle's MEM containing 10% FBS. After overnight incubation, medium was replaced with Eagle's MEM containing several concentrations of FBS. After 6 days, cells harvested by trypsinization were counted with a Coulter counter.

As shown in FIG. 3, cells died at a high concentration (at least 60%) of unenriched FBS (Whole FBS), but not in the UF-FBS supplemented with MEM. In addition, cell growth was suppressed in enriched FBS as the concentration was increased. Nevertheless, the cells remained viable, suggesting MEM contained molecules that prevented cell death. Among the vitamins and amino acids tested, only the latter showed this rescue effect. One half to fourfold MEM equivalent of amino acids rescued TIG-1 cells from serum-induced cell death (data not shown). We measured the concentration of each amino acid in FBS. Among essential amino acids, L-cysteine or L-cystine and arginine were of less concentration in FBS as compared to those in MEM, which were 8–15 vs. 24 and 1–6 vs. 126, respectively. To identify the amino acids responsible for the rescue effect, each of the 20 L-amino acids involved in protein synthesis and L-hydroxyproline were tested (data not shown).

Figure 4:
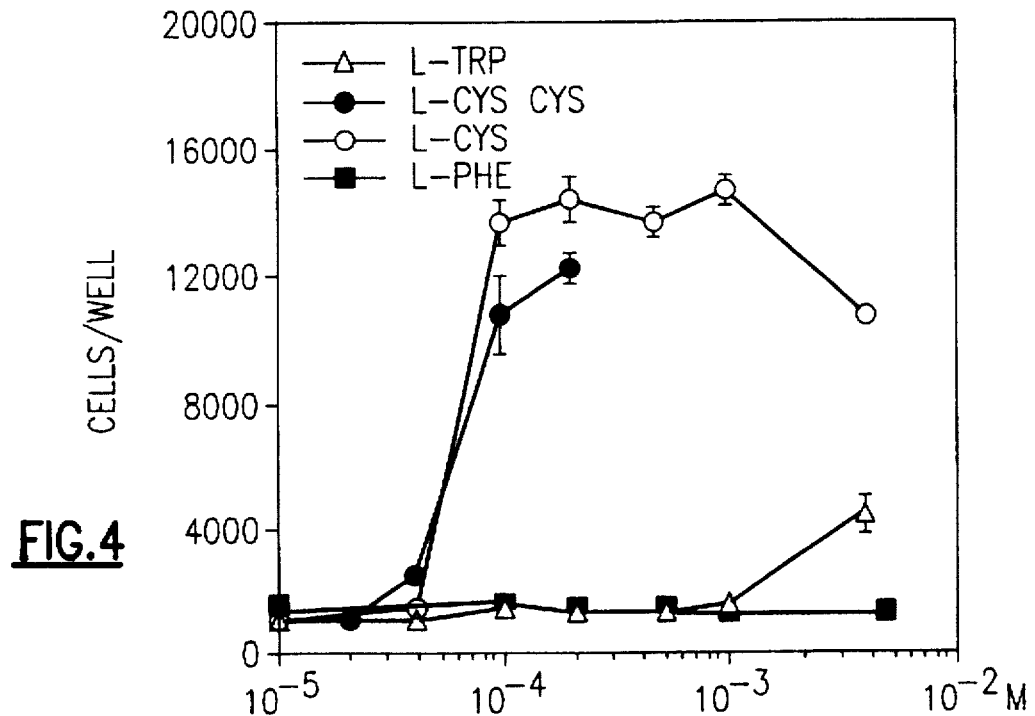
FIG. 4 is a chart illustrating rescue from serum-induced cell death by amino acids.

Rescue from serum-induced cell death by amino acids is illustrated in FIG. 4. In developing the data illustrated in FIG. 4 TIG-1 cells were seeded in 96-well microplates at a density of $5\times10^3$ cells/well in Eagle's MEM containing 10% FBS. After overnight incubation, medium was replaced with FBS containing amino acids. After 6 days, cells were counted with a Coulter counter. Only two amino acids, L-cysteine or L-cystine and L-tryptophan, showed ability to rescue cells from serum-induced toxicity (FIG. 3) With L-cysteine, cell death was completely prevented at 0.1 mM, and cells grew well at I mM. With L-cystine, whose maximum solubility is ~0.5 mM, protective effect were observed beginning at 0.05 mM (0.1 mM cysteine equivalent). In contrast, L-tryptophan was effective only at concentrations above 5 mM, and it only partially rescued the cells. Concentrations of L-cysteine higher than 5 mM sometimes inhibited cell growth. Similar to TIG-1 cells, HeLa cells and B16 cells were also protected by L-cysteine or L-cystine and L-tryptophan (data not shown).

The rate of glutathione synthesis in cultured fibroblasts is known to depend on the cystine content of the medium (Meister and Tate, 1976), and when glutathione was added to the medium of TIG-1 cells, death was prevented. This also occurred when oxidized glutathione (GSSG) was tested. There was no evidence of extracellular enzymatic reduction of GSSG or its transport into the cell. Accordingly, the rescue activity of glutathione may not be due to its ability to conjugate to other molecules via thiol linkages.

To further study the roles of cysteine and glutathione, experiments were performed as before using reducing agents, dithiols, L-amino acids, denaturants, and an active oxygen-eliminating enzyme. These reagents are listed below. Reducing agents: L-ascorbic acid, L-ascorbic acid phosphate, Mg, DL-α-tocopherol, dithiothreitol, 2-mercaptoethanol, thioglycolic acid, N-acetyl-L-cysteine, sodium dithionite, potassium ferrocyanide, thiourea. Dithiols: DL-homocysteine, 5,5'-dithiobis(2-nitro benzoic acid); L-amino acids: L-tryptophan, L-methionine; chelates: ethylene diamine tetra-acetic acid and ethylene glycol bis(2-aminoethylether). Denaturants: urea, sodium dodecyl sulfate; Active-oxygen eliminating enzyme: bovine erythrocyte superoxide dismutase (SOD) (WAKO).

FIG. 1. illustrates rescue from serum-induced cell death by thiols. In developing the data shown in FIG. 1, TIG-1 cells were seeded in 96-well microplates at a density of $1\times10^4$ cells/well in Eagle's MEM containing 10% FBS. After overnight incubation, medium was removed, and 80 µl of FBS plus 20 µl of PBS containing cysteine (CYS), cystine (CYS-CYS), glutathione oxidized (GSSG), glutathione reduced (GSH), dithiothreitol (DTT), 2-mercaptoethanol (2-ME), sodium dithionite (DTN), thioglycolic acid (TGA), DL-homocystine (DL-HC), N-acetyl-L-cysteine (NAC), or 5,5'-dithiobis(2-nitrobenzoic acid) (DTNB) were added to each well. All reagents were tested for rescue from cell death at concentrations ranging from 10 µM to 1 mM, in some cases to 10 mM. D- and L-cystine were tested in the range of 1 µM to 100 µM, because of low solubility. After 4 days, cell number was determined by the dye elution method. Reagents were tested in concentrations from 1 pM to 1 mM or 1 µM to 10 mM, except in the case of SOD, which was tested in the range $10^1 10^4$ units/ml. Only rescue activity-positive data from independent experiments are depicted in FIG. 1. All reagents bearing SH or cleaved dithiols possessed the rescue activity, and cysteamine and cystamine also were effective in preventingcell death. In contrast, the nonthiol-reducing agents were inactive (data not shown).

Figure 5:
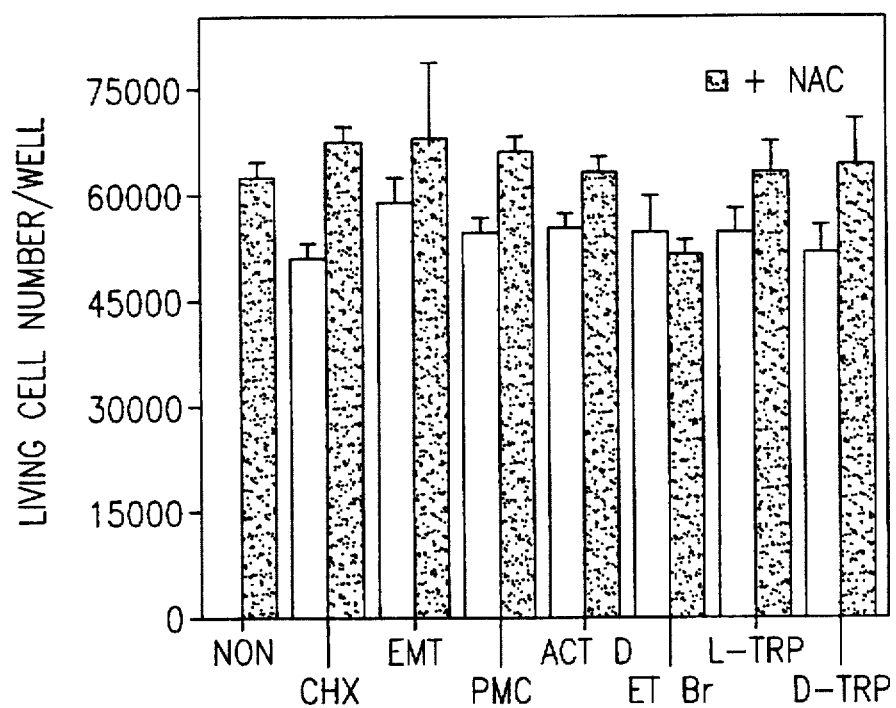
FIG. 5 illustrates rescue from serum-induced cell death by inhibitors of protein and RNA synthesis.

To determine whether death was due to apoptosis or necrosis, various inhibitors of protein synthesis and RNA synthesis were tested for the rescue activity, since it is generally accepted that in apoptosis specific protein(s) are synthesized. The procedure is explained with reference to FIG. 5. which illustrates rescue from serum-induced cell death by inhibitors of protein and RNA synthesis. The ordinate in FIG. 5 represents the number of viable TIG-1 cells after 24 hr incubation. Open columns indicate reagent only. Striped columns indicate reagent +1 mM N-acetyl-L-cysteine (NAC). NON, PBS only; CHX, 1 µg/ml cycloheximide; PMC, 1 µgl/ml puromycin.2HCl; EMT, 1 µg/ml emetine.2HCl; L-TRP, 10 mM L-tryptophan; D-TRP, 10 mM D-tryptophan; ACT D, 10 µg/ml actinomycin D; ET Br, 25 µg/ml ethidium bromide. TIG-1 cells were seeded in 48-well microplates at a density of $3\times10^4$ cells/well in Eagle's MEM containing 10% FBS. After 3 days incubation, medium was replaced with 200 µl of FBS plus 50 µl of PBS containing each reagent. After 24 hr, the number of viable cells was determined by a hemocytometer. All the reagents were tested for rescue from cell death at concentrations ranging from 0.1 µg/ml to 10 µg/ml except for D- and L-tryptophan. Data at the most effective concentration are shown in this graph. All reagents were tested at concentrations ranging from 0.01 to 10 µg/ml, and in a separate group 1 mM NAC was added as a positive control. Protein synthesis inhibitors CHX, PMC and EMT, and RNA synthesis inhibitors ACT D and ET Br, prevented death of cells in these cultures, suggesting that serum-induced toxicity requires protein synthesis.

Inhibitors of protein and RNA synthesis protected cells against serum-induced toxicity similar to thiols, yet they never showed a growth-promoting effect. Accordingly, these inhibitors may act via a molecular mechanism different from that of thiols. To determine whether thiols inhibited protein synthesis, L-[$^{35}$S]methionine uptake into TIG-1 cultured in FBS was measured. A typical result from three independent experiments is presented in FIG. 6. To develop the data shown in FIG. 6 TIG-1 cells were seeded into a 24 well-multiplate at a half-confluency (about $6\times10^4$ cells/well), and medium was replaced with FBS containing 20 µCi L-[$^{35}$S] methionine. After incubation for each indicated time, cells were lysed and macromolecules were precipitated with TCA. Precipitates were dissolved in buffer and counted by liquid scintillation. TIG-1 cells cultured in FBS showed substantial uptake of L-[$^{35}$S]methionine, suggesting that cells vigorously synthesized protein prior to death. L-[$^{35}$S] methionine uptake into TIG-1 cells in all three experiments was completely inhibited by 1 µg/ml CHX and partially inhibited by 5 mM L-tryptophan (30–50%). By comparison, 1 mM NAC did not inhibit L-[$^{35}$S]methionine uptake.

Figure 7A:
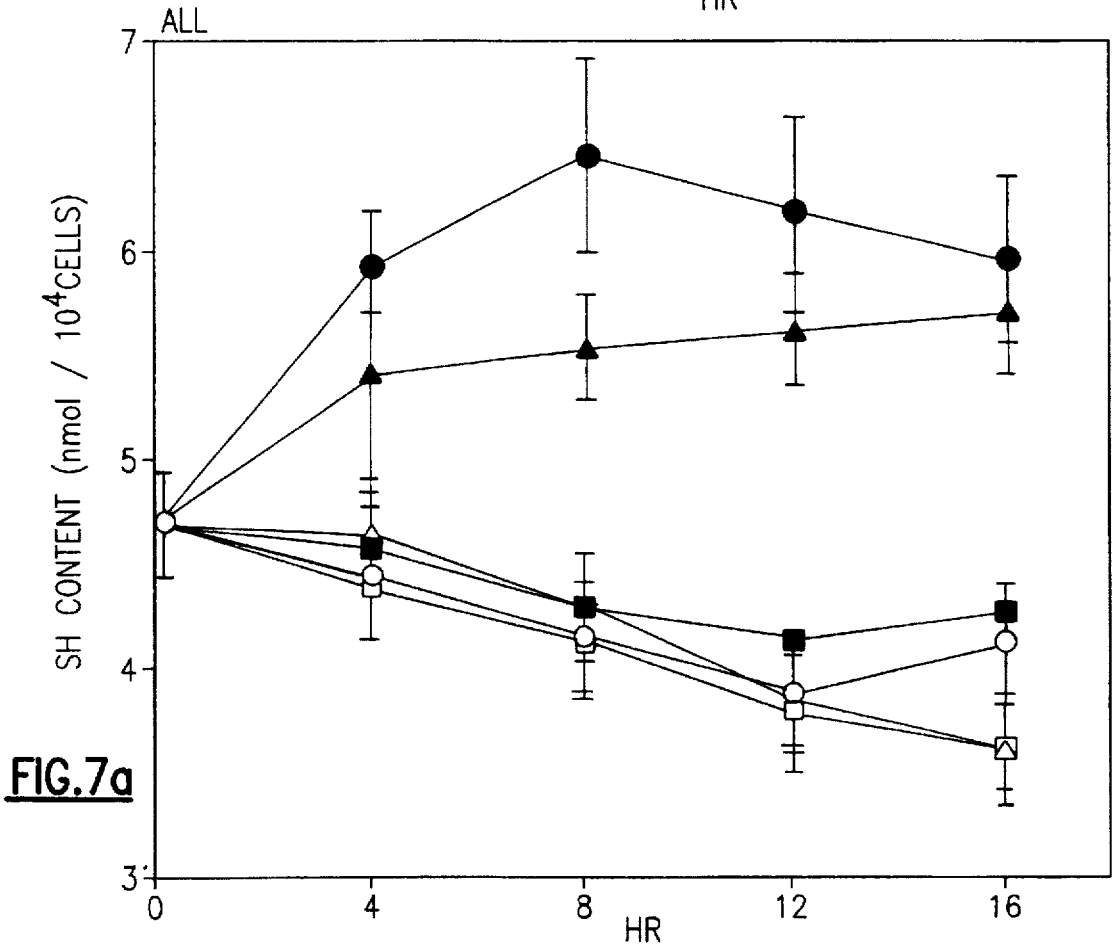
FIGS. 7a and 7b are charts respectively illustrating total thiol content and ethanol-soluble thiol content of cultured cells following incubation in the presence of various reagents.
Figure 7B:
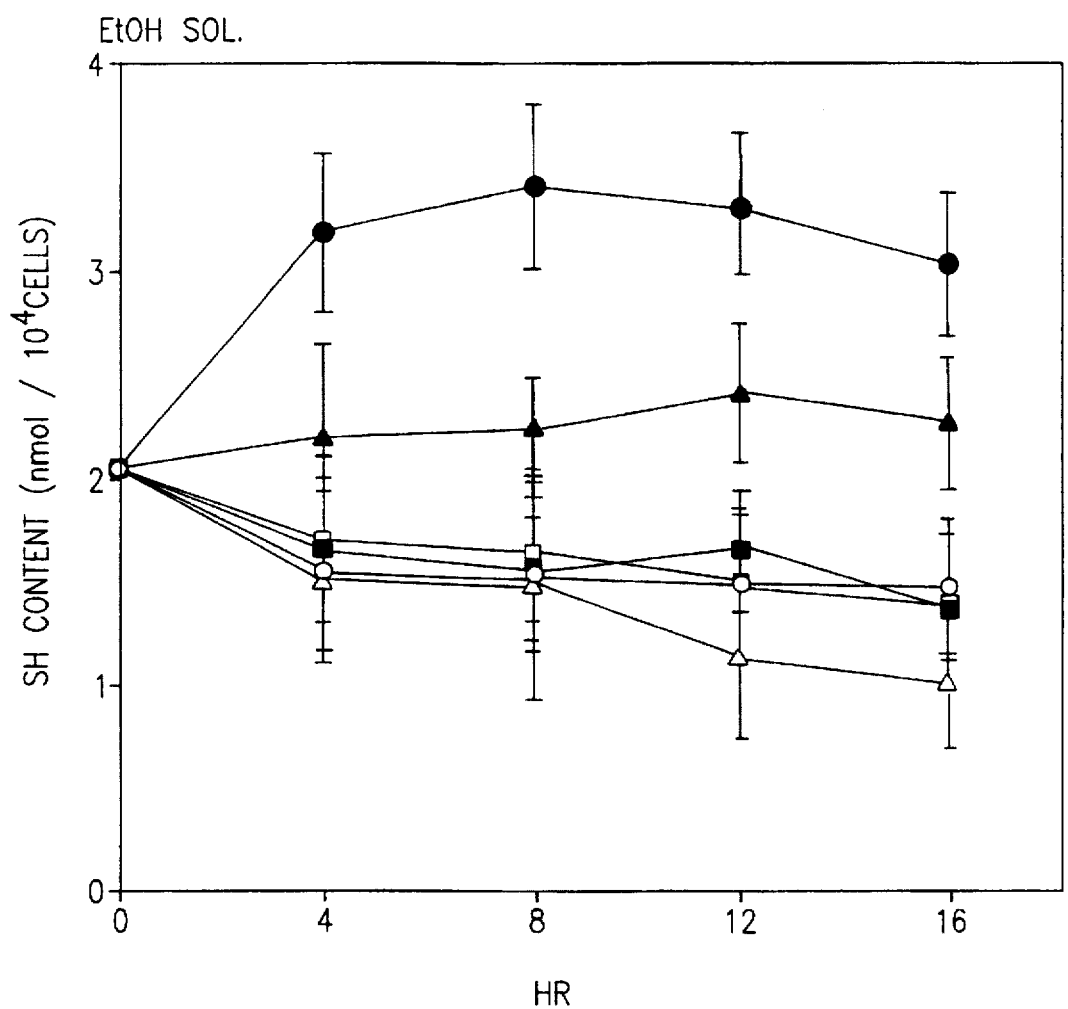

We interpreted these results to indicate that supplemental thiols prevent cell death by maintaining intracellular thiol levels. We found, however, that acid-soluble thiol content of TIG-1 cells cultured in FBS quickly decreased whether or not the medium was supplemented with thiol (data not shown). Thereafter, total and ethanol-soluble thiol content were measured in subsequent experiments. As shown in FIGS. 7a and 7b, both thiol contents were conservative when 1 mM NAC was added to FBS, whereas protein synthesis inhibitor CHX did not affect thiol content either total and ethanol-soluble. The following procedure was followed in developing the data plotted in FIGS. 7a and 7b: After several hours incubation in test medium, cells were lysed in 1% SDS, 0.02% EDTA, 50 mM Tris-HCl (pH.8.2). Either the total lysate or the lysate after precipitation of macromolecules by x3 volume of ethanol (ethanol-soluble) was dyed with 20 mM DTNB. Absorbance at 415 nm was measured by microplate reader 3550 (Bio Rad). Concentration of thiol was calculated by comparison to a GSH standard. Thiol content was expressed as SH mol/living cell number. FIGS. 7a and 7b are to be interpreted in conjunction with the following key:

| ● | 10% FBS containing Eagle's MEM; | ▲ | FBS + 1 mM NAC; |
|---|---|---|---|
| | | ○ | 1 µg/ml CHX; |
| □ | Hanks's balanced solution; | ■ | FBS + 1 mM L-TRP. |
| △ | FBS; | | |

Another distinguishing feature of apoptosis, namely, DNA fragmentation, was evaluated by agarose gel electrophoresis of low molecular weight DNA from dying cells at various stages of serum toxicity. Living cell ratios were measured by the method of trypan blue exclusion, as illustrated in FIG. 8. The chart shown in FIG. 8 reflects the result of the following procedure: TIG-1 cells were seeded into a 35 mm culture dish at a density of $2 \times 10^5$ cells/dish. When the density reached $3.5 \times 10^5$ cells/dish, medium was replaced with FBS. After the incubation for each indicated time, cells were harvested with 0.1% trypsin in CMF-PBS, and 0.5% trypan blue in PBS was added. Cells that excluded the dyed were counted as living with a hemocytometer. Results are expressed as the means (i SE) of four independent determinations. Until 6 hr of the serum treatment, the cells appeared morphologically viable and were not stained by trypan blue. At that point, viability declined steeply, and all cells were dead by 12 hr. DNA fragments (ladder) appeared at 6 hr of the treatment before the plasma membrane breakdown, and they persisted until 12 hr. Electrophoresis of DNA fragments of dying cells (not shown) was conducted using 2.6% agarose-gel. The maximal length of the DNA ladder was relatively small (<0.7 kbp), and the space between rungs of the ladder was slightly smaller than the 0.2 kbp value reported for the DNA ladder usually observed during apoptosis (Kerr et al., 1972; Wyllie et al., 1980; Ellis et al., 1991; Raff, 1992; Eastman, 1993). Nevertheless, DNA fragmentation proceeded morphological change by a few hours, and RNA and protein synthesis inhibitors prevented cell death, consistent with the view that serum-induced toxicity is a type of apoptosis.

In the present study, we observed that serum-induced toxicity was prevented with thiol (SH)-related molecules. Disulfide, D-cysteine or D-cystine, and DTNB were effective in rescuing cells despite the fact that these compounds are not normally present in cells and do not function as reducing agents in medium. In addition, dithionite, a reducing disulfide, was protective. The findings suggest that these reagents may promote efficient cellular utilization of SH by dithiol exchange or by a reaction involving chemical reduction. The standard cell culture system is an oxidative environment, where SH is oxidized to form dithiol. SH-compounds like cysteine and glutathione in serum are, therefore, able to form dithiol homo-dimers or mixed disulfides with low molecular weight thiols and proteins. In contrast, cells find little use for mixed disulfides. However, if molecules such as L-cysteine, reduced glutathione, or L-cystine are produced through exchange or reducing, they may be readily used by cells, resulting in promotion of intracellular SH metabolism.

Intracellular thiol levels were decreased in high concentrations of serum, and addition of thiols reversed the decline. Thiol content began to decrease several hours prior to plasma membrane breakdown, and this suggests that the lowering of thiol content was a causal factor in serum-induced cell death rather than a result. It was not, however, the only cause of death, because Hank's balanced solution did not induce death even though thiol content was reduced as in the case of cells cultured in FBS. Protein synthesis inhibitors prevented cell death, but they had no effect on intracellular thiol content, suggesting that protein synthesis was necessary for serum-induced toxicity.

Figure 6:
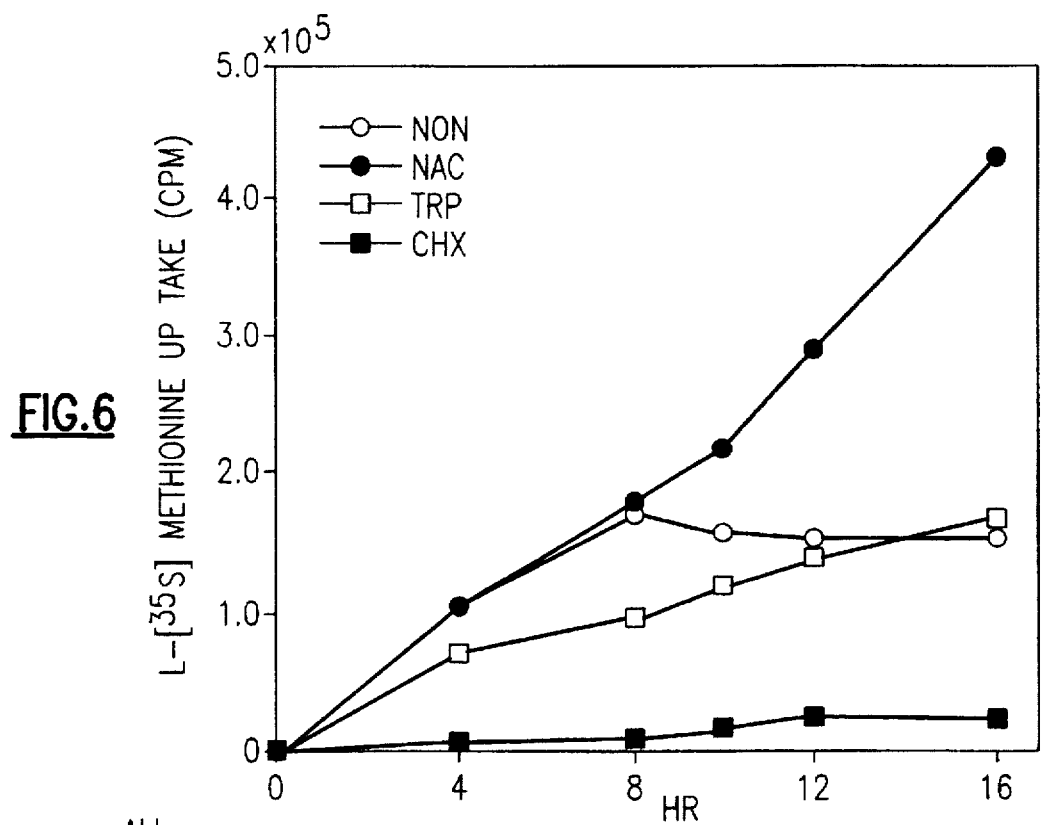
FIG. 6 is a chart illustrating the effect of protein and RNA synthesis inhibitors on methionine uptake in cultured cells.

Taken as a whole, the evidence is consistent with two hypotheses for serum-induced cell death, schematically illustrated in FIGS. 9a and 9b. The first is that a decrease in thiol content directly induces synthesis of proteins required for programmed cell death (FIG. 9a). The second is that a decrease in thiol content affects a variety of intracellular processes that occur during cell death including protein synthesis (FIG. 9b). Whether either of these hypotheses can be experimentally verified remains to be determined. During protein synthesis, de novo RNA synthesis may not be necessary, since RNA synthesis inhibitors only partially protected against death of HeLa cells and low density cultures of TIG-1 cells. High concentrations of L- and D-tryptophan showed equal ability to rescue cells. To our knowledge, inhibition of protein synthesis by tryptophan has not been reported, yet our preliminary study showed that L-tryptophan incompletely inhibited L-[$^{35}$S]methionine uptake by cultured TIG-1 cells (FIG. 6). This may indicate that L- and D-tryptophan can act as protein synthesis inhibitors in some cases.

Addition of exogenous thiol compounds maintained the intracellular level of total thiol, including the protein fraction against depletion by serum-induced toxicity. The level of acid-soluble thiol was, however, not always restored by the addition, whereas that of ethanol soluble thiol moderately increased. Ethanol is known to solubilize short peptides more efficiently than TCA, and this may be the reason why the ethanol soluble thiol level was higher. These results suggest that supplemental thiol was predominantly incorporated into protein fractions that maintained the total thiol level.

It is possible that thiols contained in protein fractions may act as modifiers of cysteine residues. For example, some enzymes require modification of their cysteine residues by glutathione for activation (Ziegler, 1985). Serum-induced toxicity may reflect such a functional disorder caused by a shortage of thiols.

A second major observation was that DNA was cleaved into fragments beginning a few hours before plasma membrane breakdown. The electrophoretic behavior of the DNA differed from ordinary apoptosis in that the fragments were smaller, and sometimes the DNA appeared to be randomly digested, showing a smeared pattern rather than discrete bands. Nevertheless, a characteristic feature of apoptosis was evident, namely, DNA fragmentation prior to membrane disintegration.

Literature Cited

Abrams, J. M., White, K., Fessler, L. I., and Steller, H. (1993) Programmed cell death during Drosophila embryogenesis. Development, 117:29–43

Bissonnefte, R. P., Echeverri, F., Mahboubi, A., and Green, D. R. (1992) Apoptotic cell death induced by c-myc is inhibited by bcl-2. Nature, 359:552–554.

Cohen, J. J., Duke, R. C., Fadok, V. A., and Sellins, K. S. (1992) Apoptosis and programmed cell death in immunity. Ann. Rev. Immun., 10:267–293.

Coles, H. S. R., Burne, J. F., and Raff, M. C. (1993) Large-scale normal cell death in developing rat kidney and its reduction by epidermal growth factor. Development, 118:777–784.

Cowan, W. M., Fawcett, J. W., O'Leary, D. D. M., and Stanfield, B. B. (1984) Regressive events in neurogenesis. Science, 225:1258–1265.

Driscoll, M. (1992) Molecular genetics of cell death in the nematode *Caenorhabditis elegans*. J. Neurobiol., 23:1327–1351.

Eastman, A. (1993) Apoptosis: A product of programmed and unprogrammed cell death. Toxicol. App. Pharmacol., 121:160–164.

Ellis, R. E., Yuan, J., and Horvitz, H. R. (1991) Mechanisms and functions of cell death. Ann. Rev. Cell Biol., 7:663–698.

Evan, G. I., Wyllie, A. H., Gilbert, C. S., Liftlewood, T. D., Land, H., Brooks, M., Waters, C. M., Penn, L. Z., and Hancock, D. C. (1992) Induction of apoptosis in fibroblasts by c-myc protein. Cell, 69:119–128.

Fanidi, A., Harrington, E. A., and Evan, G. I. (1992) Cooperative interaction between c-myc and bcl-2 proto-oncogenes. Nature, 359:554–556.

Gougeon, M. L., and Montagnier, L. (1993) Apoptosis in AIDS. Science, 260:1269–1270.

Henderson, S., Rowe, M., Gregory, C., Croom-Carter, D., Wang, F., Longnecker, R., Kieff, E., and Rickinson, A. (1991). Induction of bcl-2 expression by Epstein-Barr virus latent membrane protein 1 protects infected B cell from programmed cell death. Cell, 65:1107–1115.

Hengartner, M. O., Ellis, R. E., and Horvitz, H. R. (1992) Caenorhabditis elegans gene ced-9 protects cells from programmed cell death. Nature, 356:494499.

Hori, T., Kashiyama, S., Oku, N., Hayakawa, M., Shibamoto, S., Tsujimoto, M., Nishihara, T., and Ito, F. (1988) Effect of tumor necrosis factor on cell growth and expression of transferrin receptors in human fibroblasts. Cell Struct. Func., 13:425433.

Kerr, J. F. R., Wyllie, A. H., and Currie, A. R. (1972) Apoptosis: A basic biological phenomenon with wide-ranging implications in Tissue kinetics. Br. J. Cancer, 26:239–257.

Kurita, T., and Namiki, H. (1993a) Serum induced cell death. Zool. Sci., 10:431–438.

Kurita, T., and Namiki, H. (1993b) Comparison of cytotoxicity among sera from various sources. Cytologia, 58:445452.

McConkey, D. J., Orrenius, S., and Jondal, M. (1990) Cellular signalling in programmed cell death (apoptosis). Immunol. Today, 11:120–121.

Meister, A., and Tate, S. S. (1976) Glutathione and related y-glutamyl compounds: Biosynthesis and utilization. Ann. Rev. Biochem., 45:599–604.

Meyaard, L., Otto, S. A., Jonker, R. R., Mijnster, M. J., Keet, R. P. M., and Miedema, F. (1992) Programmed death of cells in HIV-1 infection. Science, 257:217–219.

Oppenheim, R. W. (1991) Cell death during development of the nervous system. Ann. Rev. Neurosci., 14:453–501.

Raff, M. C. (1992) Social controls on cell survival and cell death. Nature, 356:397–399.

Saunders, J. W. (1966) Death in embryonic system. Science, 154:604–612.

Truman, J. W. (1984) Cell death in invertebrate nervous system. Ann. Rev. Neurosci., 7:171–188.

Wyllie, A. H., Kerr, J. F. R., and Currie, A. R. (1980) Cell death: The significance of apoptosis. Int. Rev. Cytol., 68:251–306.

Yonish-Rouach, E., Resnitzky, D., Lotem, J., Sachs, L., Kimchi, A., and Oren, M. (1991) Wild-type p53 induces apoptosis of myeloid leukemic cells that is inhibited by interleukin 6. Nature, 352:345–347.

Ziegler, D. M. (1985) Role of reversible oxidation-reduction of enzyme thiols-disulfides in metabolic regulation. Ann. Rev. Biochem., 54:305–329.

While this invention has been explained with reference to the structure disclosed herein, it is not confined to the details set forth and this application is intended to cover any modifications and changes as may come within the scope of the following claims:

What is claimed is:

1. A method of accelerating serum induced cell death in a cell system comprising the steps of:

providing a medium comprising a cytotoxic concentration of serum, said concentration being sufficient to induce cell death;

exposing a population of living cells to said serum; and exposing said cells to glycine in an amount effective to accelerate induction of death of said cells by said serum.

2. The method according to claim 1, wherein said concentration of serum is at least 60 percent.

3. The method according to claim 2, wherein said glycine has a concentration of 1 mM.

4. The method according to claim 2, wherein said living cells are human fetal lung fibroblasts.

5. The method according to claim 2, wherein said living cells are human epithelioid carcinoma cells.

6. The method according to claim 2, wherein said living cells are mouse melanoma cells.

7. The method according to claim 1, wherein said serum comprises whole fetal bovine serum having a concentration of at least 60 percent.

8. The method according to claim 7, wherein said glycine has a concentration of 1 mM.

9. The method according to claim 7, wherein said living cells are human fetal lung fibroblasts.

10. The method according to claim 7, wherein said living cells are human epithelioid carcinoma cells.

11. The method according to claim 7, wherein said living cells are mouse melanoma cells.

* * * * *

UNITED STATES PATENT AND TRADEMARK OFFICE
CERTIFICATE OF CORRECTION

PATENT NO. : 5,792,479
DATED : August 11, 1998
INVENTOR(S) : Hideo Namiki, et al.

It is certified that error appears in the above-identified patent and that said Letters Patent is hereby corrected as shown below:

Col. 1, Line [75], inventor: add -- Takeshi Kurita -- and insert --both of--.

Col. 3, Line 23, delete -- and10 -- and insert -- and 10 --.

Col. 5, Line 24, delete -- 5-5,5' -- and insert -- 5,5' --.

Col. 5, Line 39, delete -- I mM -- and insert -- 1 mM --.

Col. 6, Line 47, delete -- NEM -- and insert -- NEAA --.

Col. 7, Line 44, delete -- L-[$^{35}$] -- and insert -- L-[$^{35}$S] --.

Col. 9, Line 11, delete -- I mM -- and insert -- 1 mM --.

Col. 9, Line 58, delete -- 1 pM -- and insert -- 1 $\mu$M --.

Col. 9, Line 60, delete --$10^1 10^4$-- and insert -- $10^1 - 10^4$ --.

Col. 9, Line 64, delete --preventingcell-- and insert -- preventing cell--.

Col. 10, Line 10, --$\mu$gl/ml-- and insert --$\mu$g/ml--.

Col. 11, Line 8, delete -- + 1 -- and insert --+ 10--.

UNITED STATES PATENT AND TRADEMARK OFFICE
CERTIFICATE OF CORRECTION

PATENT NO. : 5,792,479
DATED : August 11, 1998
INVENTOR(S) : Hideo Namiki, et al.

It is certified that error appears in the above-identified patent and that said Letters Patent is hereby corrected as shown below:

Col. 11, Line 25, delete -- (i SE) -- and insert --(± SE)--.

Col. 12, Line 23, delete -- L-[$^{35}$S] -- and insert --L-[35S]--.

Col. 12, Line 58, delete --Bissonnefte-- and insert --Bissonnette--.

Col. 13, Line 13, delete --Liftlewood-- and insert -- Littlewood--.

Col. 13, Line 29, delete --494499-- and insert --494-499--.

Col. 13, Line 34, delete --425433-- and insert --425-433--.

Col. 13, Line 43, delete --445452-- and insert --445-452--.

Signed and Sealed this

Eleventh Day of April, 2000

Q. TODD DICKINSON

*Attest:*

*Attesting Officer*       *Director of Patents and Trademarks*